United States Patent [19]
Heidmueller

[11] Patent Number: 5,281,230
[45] Date of Patent: Jan. 25, 1994

[54] EXTRACTOR

[76] Inventor: Harald Heidmueller, Heidenrichstrasse 10, 5000 Koeln 80, Fed. Rep. of Germany

[21] Appl. No.: 888,706

[22] Filed: May 27, 1992

[51] Int. Cl.$^5$ .......................... A61B 17/00; A61B 19/00
[52] U.S. Cl. ........................................ 606/127; 606/1; 606/205; 606/207; 606/208; 606/128; 606/206; 604/802
[58] Field of Search .................... 606/50–52, 606/108, 107, 119, 110, 121–124, 127, 170, 205–210, 128; 294/3, 119; 604/902

[56] References Cited

U.S. PATENT DOCUMENTS

| | | | |
|---|---|---|---|
| 804,229 | 11/1905 | Hutchinson | 606/206 |
| 1,680,490 | 8/1928 | Wappler | 606/127 |
| 1,813,902 | 7/1931 | Bovie | 606/52 |
| 4,054,143 | 10/1977 | Bauer | 606/52 |
| 4,096,678 | 1/1990 | Ogawa | 606/170 |
| 4,509,517 | 4/1985 | Zibelin | 606/127 |
| 4,607,620 | 8/1986 | Storz | 606/206 |
| 4,632,110 | 12/1986 | Sanagi | 606/207 |
| 4,662,371 | 5/1987 | Whipple et al. | 606/170 |
| 4,865,030 | 9/1989 | Polyak | 606/127 |
| 4,881,550 | 11/1989 | Kothe | 604/22 |
| 4,957,505 | 9/1990 | McDonald | 606/206 |

FOREIGN PATENT DOCUMENTS

| | | | |
|---|---|---|---|
| 2226495 | 1/1973 | Fed. Rep. of Germany | 606/207 |
| 3632786 | 3/1988 | Fed. Rep. of Germany | 606/127 |
| 3920706 | 1/1991 | Fed. Rep. of Germany | 606/205 |
| 2355521 | 2/1978 | France | 606/52 |
| 0104674 | 5/1924 | Switzerland | 606/106 |
| 0005255 | of 1825 | United Kingdom | 606/127 |

Primary Examiner—Stephen C. Pellegrino
Assistant Examiner—Glenn Dawson
Attorney, Agent, or Firm—Diller, Ramik & Wight

[57] ABSTRACT

An extractor for gallbladders and appendices, comprising a protective guiding tube for insertion into the peritoneum of a patient, a gripping means provided at the front end of the protective guiding tube and comprising at least two bowls which are adapted to be opened and closed like tongs and which, in the closed state, form a rotational body extending longitudinally in the direction of the protective guiding tube, and an operating means for opening and closing the bowls and projecting from the rear end of the protective guiding tube, the transimission elements of the operating means lie within the protective guiding tube and extend therethrough.

20 Claims, 2 Drawing Sheets

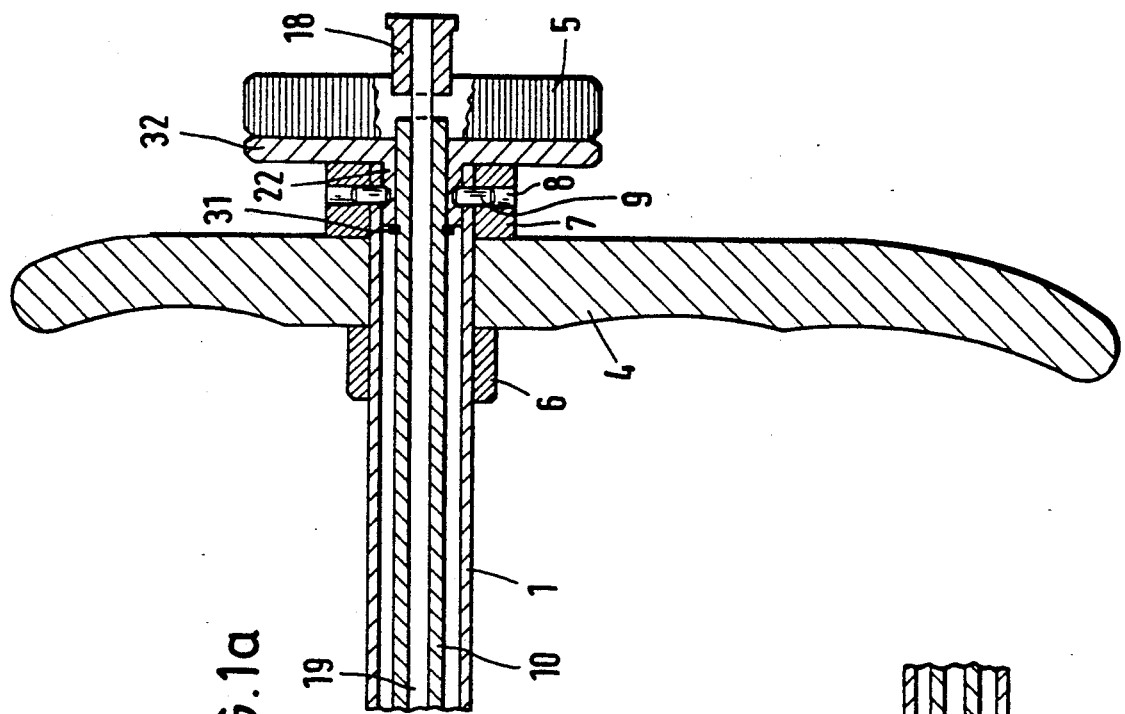
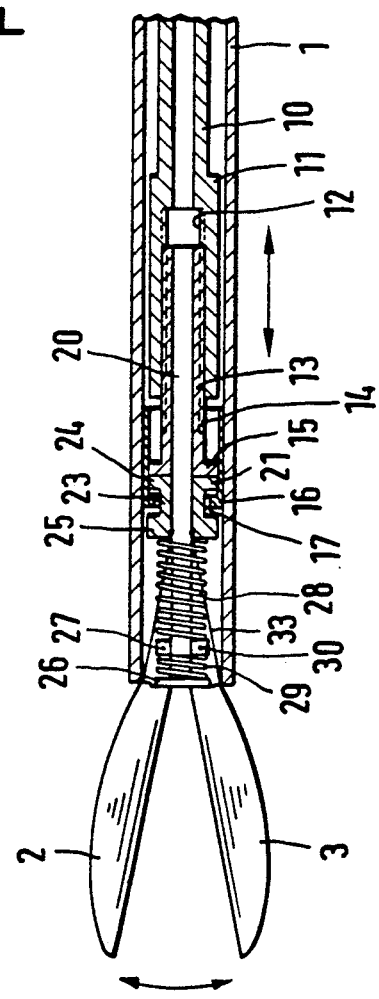
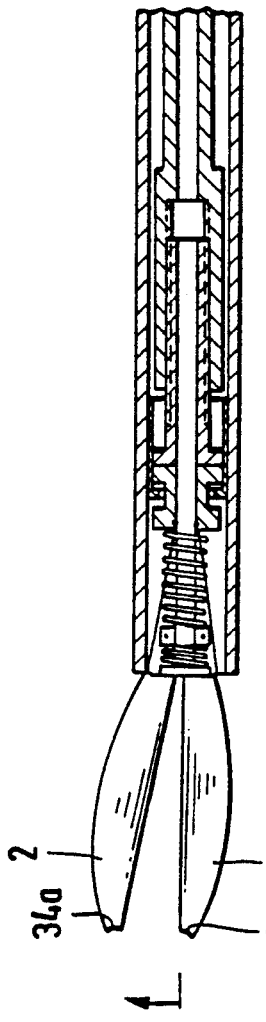
FIG.1a
FIG.1b

EXTRACTOR

BACKGROUND OF THE INVENTION

The present invention refers to an extractor for extracting gallbladders, appendices, myomas, cysts, resected portions of the intestines and the like.

Such organs and similar parts are presently removed from the body of a patient through the opened abdominal cavity. Due to the opening of the abdominal cavity and the possibility of opened body tissue coming into contact with the parts to be removed, a high risk of infection is given. Gallbladders and appendices, as well as parts of the great intestine or the small intestine, contain a lot of germs and bacteria which may cause dangerous infections when coming into contact with fascial tissue, fatty tissue or cutaneous tissue.

German Patent 39 20 706 describes a biopsy device for biopsy on a living body. In a guiding catheter, which usually is soft or flexible, a catheter sheath is provided which extends out of the catheter and has a forceps means at the front end, which has two bowl-shaped jaws. By longitudinally displacing an operating skein, the jaws of the forceps can be opened and closed to cut off and grip tissue. The contents held between the two jaws may be looked at through an endoscope.

From U.S. Pat. No. 4,881,550, another biopsy device is known, which has a cutting device comprising two arcuate cutting blades and which is provided at the front end of a tube. For cutting, the cutting device is drawn to the tube, the guiding edges of the cutting blades being pulled into recesses of the tube so as to close the cutting blades and to sever the tissue. The cut off tissue is sucked off through the tube. The cutting blades can only cut tissue, yet, they cannot enclose organs, trap them in an encapsulating manner and cut them off circumferentially.

SUMMARY OF THE INVENTION

It is an object of the present invention to provide an extractor that is suitable for taking out complete parts of the body, such as organs or stones.

In the extractor of the present invention, the bowls are closed by drawing them towards the front end of the rigid tube. Thus, the closing mechanism does not include guides and levers for the forceps, but it is based on the fact that the bowls, which do not fit into the tube when they are spread apart, are pulled into the tube either partially or completely so that a great closing force can be exerted with simple means. Thus, it is ensured that the organ or the part of the body to be extracted is received in the bowls all of the time and that the organ is safely severed by the edges of the bowl. In addition, the organ is sucked into the capsule via the suction channel, the bowl-shaped walls of the capsule being closed.

It is of particular importance that a secure closing of the bowls is done with great strength so that the contents of the capsule cannot prevent the closing.

Due to the great closing force, the bowls may even destroy gall stones or other stones. The extractor allows to draw in and extract entire organs or stones that come in larger pieces without these organs or stones coming into contact with other parts of the body. The extractor allows to close the capsule securely and firmly, even if the contents is too big. The organ to be removed can be severed and removed without being destroyed within the body. The destruction is done only within the capsule, if at all.

The effect intended by the invention is that the parts to be removed can be entirely enclosed within the closed bowls and be removed through a small operation opening, the bowls substantially forming a closed longitudinal rotational body, the cross section of which does not have to exceed the cross section of the protective guiding tube, or does so only slightly. Should a use in laparoscopic surgery be intended, a simple stop may be provided at the end of the protective guiding tube that delimits the insertion into a trocar. If no trocar is to be used, the rear end of the protective guiding tube should advantageously be provided with a supporting means being substantially perpendicular thereto, which may be positioned on the exterior of the abdomen.

In a particularly advantageous embodiment of the instrument, the operating means has a central inner opening extending over the entire length of the instrument, through which a further instrument, such as a cannula or the like, may be advanced up to the opened bowls. For example, the gall liquid can be sucked off by means of a puncture needle prior to the extraction of the gallbladder. Similarly, it is possible to insert dilation catheters or bougies for the bouginage or the dilation of the choledochus, for example. The above instruments with very small outer cross sections in the closed state, for example a forceps for pulling the prepared part into the area of the bowls prior closing the same, are known per se.

Depending on the type of the further instruments to be inserted, the rear end of the operating means should preferably be provided with a gas- or liquid-tight connector assembly. In surgery of the laparoscopic type, with or without a trocar, the same may be used to connect a pressurizing means.

The at least two or more, i.e. up to four, bowls may comprise pairs of a stationary and a movable bowl-shaped member, for example. Similarly, one may also provide two bowls spreadable with respect to the longitudinal axis of the protective guiding tube. In an advantageous embodiment, the bowls are maintained in their open position by the action of a resilient force and may be closed by axially or rotatingly operating the transmission elements through a rear operating means. This may be done by a corresponding bayonet handle or a twisting assembly that converts a rotational movement into an axial movement through a spindle assembly or cam curves.

In a particularly advantageous embodiment, the bowls may be drawn into the protective guiding tube at least partially, preferably entirely, when in the closed state. In such an embodiment, the instrument is particularly suitable for laparoscopic surgery, also without a trocar, since the closed bowls do not or only slightly exceed the cross section of the tube when drawn in partially or entirely, and they may be inserted through a previously pierced opening for surgery, and since the protective guiding tube afterwards is sealingly positioned in the opening and may itself be used for pressurizing or maintaining a pressure.

When removing a correspondingly exposed and severed gallbladder, the bowls of the present invention simultaneously have the effect that possibly existing gall stones are crushed upon closing the bowls. It is possible to generate particularly great forces by drawing the bowls into the protective guiding tube. Twisted off appendices and eposed myomas can also be entirely enclosed. To this avail, the bowls may partially engage each other. However, it is most advantageous to draw the bowls completely into the protective guiding tube. The form of the bowls allows their removal through the surgical opening in the peritoneum, also if the bowls are not completely but only partially closed.

In an advantageous manner, the closing of the bowls is effected against the resilient forces by partially or completely drawing the bowl bodies into the protective guiding tube. Yet, other closing mechanisms are possible, which may nevertheless be combined with a device for retracting the closed bowls into the protective guiding tube.

The bowls with the operating means may be disassembled from the protective guiding tube at the rear, in particular when using a bayonet lock. This facilitates cleaning and allows the implementation of different bowl shapes coresponding to the surgical needs.

The following is a detailed description of an embodiment of the present invention with reference to the accompanying drawings.

BRIEF DESCRIPTION OF THE DRAWINGS

FIG. 1a is an embodiment of the instrument according to the present invention with two movable bowls;

FIG. 1b is an instrument according to the present invention with one movable bowl.

DESCRIPTION OF THE PREFERRED EMBODIMENT

Figure 2:
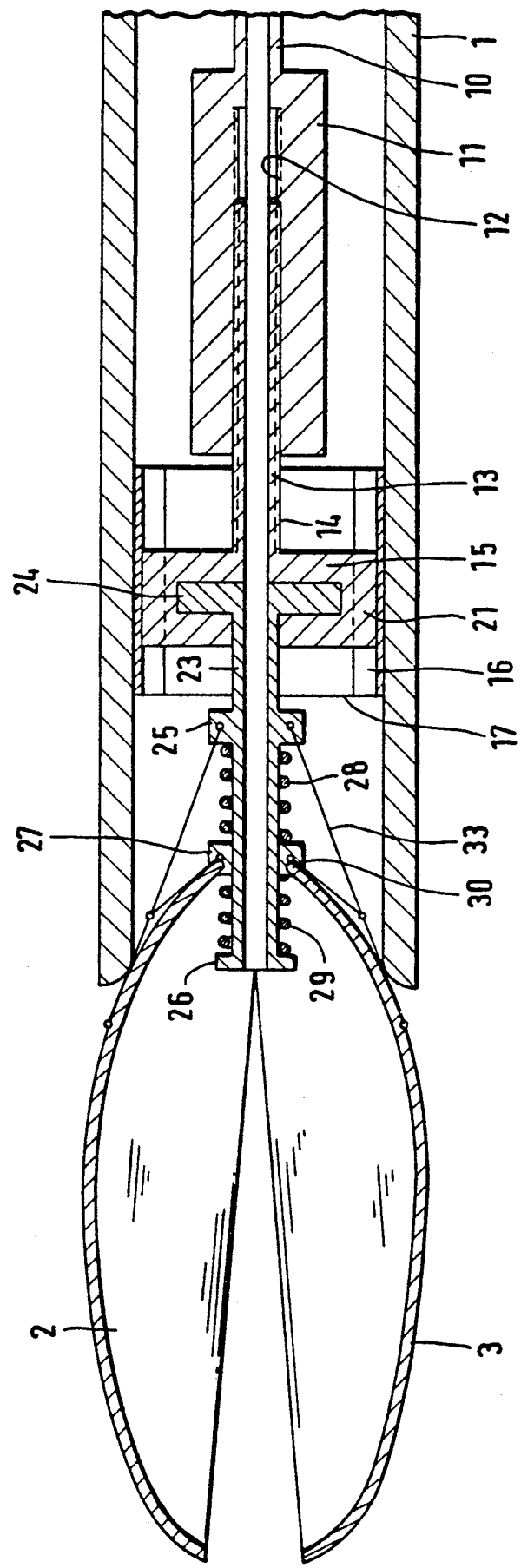
FIG. 2 shows details of the operating means for the bowls.

In FIG. 1a, the instrument is shown, respectively, comprising a protective guiding tube 1, two bowls 2, 3 adapted to be spread apart from each other, a supporting plate 4 and an operating disc 5. Guiding projections 6, 7 are fixedly arranged at the plate 4 which has guiding slots 8 of a bayonet lock provided therein, which are engaged by pins 9 radially set into a bearing bushing 22. The bearing bushing 22 is axially fixed on an operating sleeve 10 by means of a securing ring 31 and has a rear collar 32 with which the bayonet lock may be operated. The rotatable operating sleeve 10 is set into the operating disc 5 so as to rotate therewith. Fastened at the front end thereof, there is a sleeve portion 11 with an internal thread 12. A sleeve portion 13 with an external thread 14 is screwed into the same. The latter portion has an enlargement 15 at the front end, which is provided with guiding wedges 21 engaging longitudinal grooves 16 of a sleeve 17 fixed in the protective guiding tube 1. A further sleeve 23 (FIG. 2) carried by the sleeve 13 so as to be carried therewith, the sleeve 23 having an enlarged base portion 24 and two fixed collar portions 25, 26, an interposed sliding sleeve 27 being guided on that sleeve 23. The sliding sleeve 27 is supported on the sleeve 23 between the collar portions 25, 26 by compression springs 28, 29. On the sliding sleeve 27, the bowls 2, 3 are pivotably supported on pivot axles 30. A spreading mechanism for the bowls 2, 3 further comprises guides or levers 33 engaging at the collar portion 25, on the one hand, and the exterior of the bowls 2, 3, on the other hand, and spreading the same outward when the sliding sleeve 27 is displaced to the left as viewed in FIG. 2. Thus, by rotating the sleeve 10 with the operating disc 5, the sleeve portion 13, held against rotation therewith, is displaced axially, whereby the bowls 2, 3 are spread or closed, as will be described in the following. With the bayonet lock, the bowls 2, 3 and the transmission elements may be removed rearwardly from the protective guiding tube 1.

On the outside, the operating disc 5 is provided with a Luer lock hub or a bayonet lock 18 with a trumpet valve for the pressure- and fluid-tight connection of further instruments.

An inner opening 19 extends over the entire length of the sleeve 10, and an inner opening 20 extends over the entire length of the sleeves 13, 23, through which, starting from the hub member 18, an instrument, such as a forceps or the like, an injection or a puncture needle, a cannula or the like, is inserted up to the area of the bowls 2, 3.

The bowls 2, 3 of FIG. 1a may be spread commonly. Of the bowls 2, 3 of FIG. 1b, only the bowl 2 is movable; these bowls have cut-outs 34a, 34b at the front for the passage of a vessel when the bowls are closed.

FIG. 2 is a broken off illustration of the front portion of the protective guiding tube 1, the front portion of the sleeve 10 with the enlarged sleeve 11 and the inner thread 12. The sleeve 13 is set into the inner thread 12 with its outer thread 14, the sleeve having guiding wedges 21 engaging longitudinal grooves 16 of the sleeve 17 set into the protective guiding tube 1 so as to rotate therewith. Thus, by rotating the sleeve 10, the sleeve 13 is displaced axially. Set into the sleeve 13 is the sleeve 23 having the enlarged base portion 24 and two fixed collar portions 25, 26, between which the sliding sleeve 27 is guided. The sliding sleeve 27 comprises pivot axles 30 oriented transversal to the longitudinal direction of the protective tube 1, on which axles the bowls are supported. The sliding sleeve 27 is held between the collar portions 25, 26 by the compression springs 28, 29, the spring 28 having a greater bias and pressing the sleeve 27 outward. The guides 33, supported at the collar portion 25 and engaging at the outside of the bowls, effect the spreading of the bowls. The spring 29 is for the compensation of play. The outsides of the bowls abut on the rounded inner opening of the protective guiding tube. When the sleeve 13 is pushed to the left and out of the protective guiding tube, the compression spring 28 urges the sliding sleeve 27 to the left and the guides pull the bowls open. When the sleeve 23 is retracted to the right, the protective guiding tube presses the bowls into their closed position against the action of the spring 28, this being facilitated by the lesser force of the spring 29.

I claim:

1. An extractor for removing organs and other parts from living bodies comprising a guide tube having axially opposite first and second end portions, a pair of relatively movable bowls disposed at said first end portion of said guide tube, a pair of generally axially aligned sleeves housed at least partially within said guide tube, thread means at first ends of each of first and second of said pair of sleeves in threaded engagement with each other, a second end of said second sleeve being adapted for manual rotation at said second end portion of said guide tube, means coupling said first sleeve to said bowls, and means for limiting said first sleeve to reciprocal nonrotary movement relative to said guide tube upon clockwise and counterclockwise rotation being manually imparted to said second sleeve second end portion to effect relative movement between said pair of bowls.

2. The extractor as defined in claim 1 wherein said coupling means includes at least one arm pivotally connected to at least one of said bowls.

3. The extractor as defined in claim 2 including suction channel means for defining a flow path through said coupling means opening into an area defined by said pair of bowls.

4. The extractor as defined in claim 2 wherein said pair of bowls are each defined by a generally concave body having a peripheral edge, and opposing portions of said peripheral edges remote from said coupling means are relieved to defined an opening for passage therethrough of a vessel, instrument or the like.

5. The extractor as defined in claim 1 including suction channel means for defining a flow path through said coupling means opening into an area defined by said pair of bowls.

6. The extractor as defined in claim 1 including channel means through said coupling means which opens into an area defined by said pair of bowls and said, second end of said first sleeve whereby an instrument or the like can be inserted through said second sleeve second end into the area defined by said pair of bowls.

7. The extractor as defined in claim 1 wherein said pair of bowls are each defined by a generally concave body having a peripheral edge, and opposing portions of said peripheral edges remote from said coupling means are relieved to define an opening for passage therethrough of a vessel, instrument or the like.

8. The extractor as defined in claim 1 including compression spring means for normally biasing said pair of bowls to an open position.

9. The extractor as defined in claim 1 including sliding collar means mounted for sliding movement upon said coupling means, and means for pivotally connecting said pair of bowls to said collar means.

10. The extractor as defined in claim 9 wherein said coupling means includes at least one arm pivotally connected to at least one of said pair of bowls.

11. The extractor as defined in claim 9 including suction channel means for defining a flow path through said coupling means opening into an area defined by said pair of bowls.

12. The extractor as defined in claim 9 including channel means through said coupling means which opens into an area defined by said pair of bowls and said second end of said first sleeve whereby an instrument or the like can be inserted through said second sleeve second end into the area defined by said pair of bowls.

13. The extractor as defined in claim 9 wherein said pair of bowls are each defined by a generally concave body having a peripheral edge, and opposing portions of said peripheral edges remote from said coupling means are relieved to define an opening for passage therethrough of a vessel, instrument or the like.

14. The extractor as defined in claim 1 including sliding collar means mounted for sliding movement upon said coupling means, means for pivotally connecting said pair of bowls to said collar means, said sliding collar means being positioned between fixed abutment means carried by said coupling means, and spring means between each fixed abutment means and said sliding collar means for biasing said sliding collar means in opposite directions.

15. The extractor as defined in claim 14 wherein said coupling means includes at least one arm pivotally connected to at least one of said pair of bowls.

16. The extractor as defined in claim 14 wherein said pair of bowls are each defined by a generally concave body having a peripheral edge, and opposing portions of said peripheral edges remote from said coupling means are relieved to defined an opening for passage therethrough of a vessel, instrument or the like.

17. The extractor as defined in claim 1 including sliding collar means mounted for sliding movement upon said coupling means, means for pivotally connecting said pair of bowls to said collar means, said sliding collar means being positioned between fixed abutment means carried by said coupling means, spring means between each fixed abutment means and said sliding collar means for biasing said sliding collar means in opposite directions, and an arm pivotally connected between at least one of said pair of bowls and said coupling means.

18. The extractor as defined in claim 1 wherein said limiting means includes an axial slot in which is reciprocally guided a rib of said first sleeve.

19. The extractor as defined in claim 17 wherein said pair of bowls are each defined by a generally concave body having a peripheral edge, and opposing portions of said peripheral edges remote from said coupling means are relieved to defined an opening for passage therethrough of a vessel, instrument or the like.

20. The extractor as defined in claim 18 wherein said pair of bowls are each defined by a generally concave body having a peripheral edge, and opposing portions of said peripheral edges remote from said coupling means are relieved to define an opening for passage therethrough of a vessel, instrument or the like.

* * * * *